(12) United States Patent
Zuziak et al.

(10) Patent No.: US 9,238,798 B2
(45) Date of Patent: Jan. 19, 2016

(54) METHOD OF PRODUCING A PHARMACOLOGICALLY STABLE FORM OF LYOPHILISED, ACTIVE PREPARATIONS OF PURIFIED BACTERIOPHAGES

(75) Inventors: Ewa Zuziak, Wroclaw (PL); Andrzej Gamian, Wroclaw (PL); Andrzej Górski, Wroclaw (PL); Tomasz Lipiński, Wroclaw (PL)

(73) Assignee: Instytut Immunologii I Terapii Doswiadczalnej Pan, Wroclaw (PL)

( * ) Notice: Subject to any disclaimer, the term of this patent is extended or adjusted under 35 U.S.C. 154(b) by 658 days.

(21) Appl. No.: 13/059,815

(22) PCT Filed: Oct. 29, 2009

(86) PCT No.: PCT/PL2009/050032
§ 371 (c)(1),
(2), (4) Date: Jul. 13, 2011

(87) PCT Pub. No.: WO2010/050833
PCT Pub. Date: May 6, 2010

(65) Prior Publication Data
US 2011/0256103 A1    Oct. 20, 2011

(30) Foreign Application Priority Data
Oct. 29, 2008    (PL) .......................... 386381

(51) Int. Cl.
*A61K 35/13*    (2015.01)
*C12N 7/00*    (2006.01)

(52) U.S. Cl.
CPC . *C12N 7/00* (2013.01); *A61K 35/13* (2013.01); *C12N 2795/10051* (2013.01); *C12N 2795/10151* (2013.01)

(58) Field of Classification Search
CPC ..................... C12N 2795/10051; C12N 7/00
USPC ...................................................... 424/93.6
See application file for complete search history.

(56) References Cited

U.S. PATENT DOCUMENTS

| 5,149,653 | A  | * | 9/1992 | Roser ............................. 435/260 |
| 2002/0127207 | A1 | * | 9/2002 | Harris et al. ................. 424/93.6 |
| 2003/0031659 | A1 | * | 2/2003 | Farmer ....................... 424/93.45 |
| 2009/0130196 | A1 | * | 5/2009 | Murthy et al. ................ 424/451 |

FOREIGN PATENT DOCUMENTS

| EP | 1854478 | * | 5/2006 | ........... A61K 39/385 |
| WO | WO 2008097115 A1 | * | 8/2008 | |

OTHER PUBLICATIONS

Jepson, 2004, Vaccine, 22, 2413-2419.*
Sorhaug et al., 1997, Trends in Food Science and Technology, 8, 35-41.*
Written Opinion of The International Searching Authority for PCT/PL2009/050032, dated Apr. 29, 2011.
International Preliminary Report on Patentability Chapter for PCT/PL2009/050032, dated May 3, 2011.
Response to Communication Pursuant to Rules 161(1) and 162 EPC submitted to the European Patent Office in connection with European Patent Application No. 09 775 370.1, dated Dec. 20, 2011.

* cited by examiner

*Primary Examiner* — Sharmila G. Landau
*Assistant Examiner* — Sheridan MacAuley
(74) *Attorney, Agent, or Firm* — Gary J. Gershik; Cooper & Dunham LLP

(57) ABSTRACT

The subject the present invention is a method of producing a pharmacologically stable form of purified and lyophilised bacteriophage preparations of increased stability and antibacterial activity, characterized in that phages produced from a bacterial lysate, for example by ultrafiltration on ultrafiltration membranes, containing a high molecular weight preparation of purified phages is stabilised most preferably with a probiotic extract in the presence or absence of neutral salts and/or organic solvents, lyophilised, characterised via HPLC chromatography, by SDS-PAGE, and bacterial lysis biological assays, and then stored under a vacuum, where the active lyophilisate is destined for phage therapy of infections and tumors.

18 Claims, No Drawings

METHOD OF PRODUCING A PHARMACOLOGICALLY STABLE FORM OF LYOPHILISED, ACTIVE PREPARATIONS OF PURIFIED BACTERIOPHAGES

The subject of the present invention is a method of producing a pharmacological, stable form of purified and lyophilised bacteriophage preparations with increased stability and antibacterial activity.

The steadily increasing number of pathogenic bacteria resistant to the antibiotics currently in use forces research on alternative antibacterial means[1]. It is thought that bacteriophages, due to their method of functioning, are a potentially ideal candidate for novel, effective bactericidal factors. The increased interest in bacteriophage therapy and/or isolated phage proteins is based on their effectiveness in treating infections untreatable with antibiotics, which has been demonstrated at several locations [2,3]. Bacteriophages possess a series of advantages over conventional antibiotics, primarily their specificity which facilitates the destruction of pathogenic bacteria without killing symbionts, due to which the subtle microbiological equilibrium of the organism is unaffected [2,4-7]. The concentration of bacteriophages in the patient's bodily fluids does not decrease after administration, but is self-regulated. The number of phages grows exponentially in the presence of bacteria and quickly drops in their absence. To date, no significant side effects have been noted during phage therapy, which may be used in patients allergic to antibiotics. Appropriately chosen and selected phages may be used in antibacterial prophylaxis, including sanitisation, i.e. of hospital chambers. Selection of resistant bacteria is also observed much less frequently, which is often the case for. Moreover, should a bacterium prove resistant to a given phage, another phage can be selected to infect it. Finally, they may be used along with antibiotics and in combined therapy. The introduction of phage therapy into widespread medical use requires the design of methods of rapidly typing appropriate phages; monitoring phage replication and their penetration of the human organism, the release of toxins by the destroyed bacteria which may lead to septic shock; removing phages from the organism [8,9]; and, finally, preparing stable, highly efficient therapeutic preparations. In a previous patent application we designed efficient procedures of culturing bacteriophages and of their purification, which made it possible to produce large quantities of pure phages, with a high activity titre, without contamination with endotoxins nor other bacterial components which would make a series of uses impossible [10]. Further research has led to original observations which are the subject of the present application, relating to the production of pharmacological forms of lyophilised active bacteriophage preparations.

To date, preparations of bacteriophages in the form of lysates of purified phages were prepared and stored in liquid form. Such a pharmacological form, though relatively stable for lysates, in purified preparations results in a rapid decrease of bacteriolytic activity. A disadvantage of liquid phage preparations is that they are an inconvenient pharmaceutical to store and use, purified phages suitable for therapeutic purposes are unstable, vial aliquoting techniques are expensive and complicated and the product requires much refrigerated storage space. The most convenient form of a drug is a solid product, i.e. a powder, tablet, granulate or lyophilisate. Such a dehydrated product is easier to produce, and is cheaper and easier to store and use. Stability and high activity levels are also required of the preparation.

The subject of the present invention is a method of producing a pharmacologically stable forms of purified and lyophilised bacteriophage preparations with increased stability and antibacterial activity, characterised in that a bacterial phage lysate, produced i.e. by ultrafiltration with a detergent on ultrafiltration membranes, containing a high molecular weight preparation of purified phages is preferentially stabilised with a probiotic extract in the presence or absence of neutral salts and/or organic solvents, which is then lyophilised and characterised via HPLC, electrophoresis in the presence of dodecyl sulphate, bacterial lysis biological assays, and is stored in a vacuum and the active powder is meant for phage therapy of infections and tumours.

The present invention solves a number of the abovementioned problems and consists firstly of the lyophilisation of purified phages in the presence of a stabilising factor such as trehalose, most preferentially a modified probiotic extract. Lyophilisation is a popular storage method, i.e. of microbiota, which facilitates long-term viability [11]. The effectiveness of the lyophilisation of microorganisms is influenced by a series of factors such as the strain of microorganism, cell shape, the stage and rate of proliferation, medium composition, cellular composition, water and lipid content, cooling and heating rates and the duration of storage [12]. The composition of the medium in which the microorganisms are suspended prior to freezing is extremely important, as the addition of appropriate substances ensures viability following lyophilisation. Initially, glycerol and dimethylsulphoxide were used to protect microbial cells against destruction caused by freezing [13,14]. Protective substances are known, both of low and high molecular weight [15], which rapidly penetrate the cell (within 30 minutes of introduction), including methanol, ethanol, ethylene glycol, propylene glycol, dimethylformamide, methylacetamide and dimethylsulphoxide; as well as slowly penetrating ones like glycol and non penetrating such as glucose, trehalose, dextran, hydroxyethyl amylose, mannitol, sorbitol, albumin, gelatin, other proteins, polyethylene glycol, or polyvinyl alcohol. As a stabilizer and protectant, sorbitol is used in microbiology at concentrations of 1-36% (usu. 9%). Depending on the microorganisms, one observes variable effectiveness of sorbitol treatment. The use of 5% mannitol on organisms yields better effects than sorbitol treatment. Glucose is used at concentrations of 1-18% (usu. 4%). Increased bacterial viability had been noted previously with the use of glucose during storage at −20° C. This has been shown to be effective for T4 bacteriophages (along with saccharose), *Enterobacter aerogenes,* yeasts and *Puccinia* spores. The drawbacks of most of the above stabilisers are that these are either liquids, or toxic (i.e. methanol), or immunogenic (i.e. albumin, gelatin), or synthetic substances usually expensive to produce, or very reactive (i.e. glukoza). Trehalose, however, is a natural protectant, occurs in plants and baker's yeast cells (*Saccharomyces cerevisiae*) and is the only disaccharide to contain two water molecules in its crystal, and is chemically inert. It is used at concentrations of 5-19% (avg. 10%) as a protectant for various viruses, *Lactobacillus bulgaricus* and other microbiota [12]. Phage preparations can be maintained in a lyophilised form, but due to the loss of activity during lyophilisation, it is recommended to use stabilizers. The present invention relates to a method of stabilising lyophilised phages with a modified probiotic extract. First, purified phage preparations are made using known methods, such as the use of a detergent and ultrafiltration membranes [10] or on an immobilised polylysine column [16], if the detergent deactivates bacteriophages. During research on the conditions for stabilising phages during lyophilisation, it was shown that among the stabilizers used, including trehalose, glucose, sorbitol or probiotic extract, the best results were obtained for trehalose and the probiotic extract. A method according to the present invention lacks the heretofore known drawbacks of lysed phage storage. Storage of bacteriophages T4, Im11 or K1 for two months in lyophilised form with trehalose or probiotic extract at various concentrations guarantees the maintenance of activity levels. After six months of storage, the activity of lyophilised phages only decreased from $8.0 \times 10^7$ pfu/ml do $4.0 \times 10^6$ pfu/ml. This activity level did not decrease and stayed unchanged, when the lyophilisate was maintained in vials under a vacuum. Phage activity was highest at a 2-4% trehalose or extract content, and decreased at higher concentrations of and trehalose, extract or other stabilizers, which means that 2% stabiliser content is an optimum. Lower titres were obtained in 1% glucose. The lowest titres were obtained using sorbitol. Though all four reagents stabilised the phages while maintaining their activity, the best result was produced by the use of 2-4% trehalose or probiotic extract. The novelty of the present invention consists of the lyophilisation and storage of phages under a vacuum in the presence of a probiotic extract as a stabilizer, which is a marked improvement over previously patented methods of storing phage preparations. The method of producing pharmacological forms is simple and requires one step, namely a solution of purified phage molecules is supplemented with a probiotic extract, usu. of *Bifidobacterium*, to a cencentration of 2%, frozen and lyophilised and apportioned into vials under a vacuum. The present invention relates to a novel pharmacological form of phages, different to any patented thus far.

Most of the patented solutions relate to phages stored as cell lysates, stable in liquid form or dehydrated lyophilisates and do not require additional stabilizers. The lysate constitutes a natural stabilizer for phages, even during lyophilisation. The need to stabilize arises following purification from a lysate, when the activity level drops drastically. The non-obviousness of the present solution is based on the fact that it does not relate to lysates, as they do not need a stabilizer, but is limited to purified phages, whose solid and liquid forms require a stabilizer. The second aspect of this solution relates to lyophilisation under a vacuum with simultaneous apportionment into vials. Vacuum packing into vials is used the long-term storage of bacteria and is preferentially used for the multi-year storage of phages purified in the presence of a stabilizer. Vacuum lyophilisation in vials is single-staged, simple, cheap, efficient and easy. The third element of the present solution is the use of a probiotic extract as a stabilizer. A simple method of preparing it comprises the use of an ethanol extract of bacterial mass treated with ammonia to remove fatty acids, where the dried aqueous phase is used as a phage stabiliser following evaporation. Strains of Bifidobacteria are known probiotics used in the food industry, cultured on corn media (17), whereas the method of extraction is simple, economical and the product is non-toxic and produced from food products.

The present invention is based on research on three phages specific for *E. coli*, laboratory phage K1 amenable to experimentation which facilitated the design of methods and tests, phage Im11 often indicated for experimental therapy as well as the polyvalent T4 phage, capable of infecting a wide spectrum of *E. coli* strains. These bacteria are the cause of many diseases. The novelty of the present invention, aside from the use of very significant, modern methods of analysing preparation purity, performed using chromatography, SDS-PAGE, bacterial wall endotoxin content evaluation such as the LAL test and chemical analyses using the GLC-MS system (Kdo method), relates to the stabilisation of lyophilised, purified phages with a probiotic extracts and storage under a vacuum. To date, sufficiently sensitive and specific methods of analysing phage purity did not exist.

The whole phage molecule produced, purified and analysed using the method according to the present invention constitutes a complete antigen set and may be needed in a series of uses in biotechnology and medicine. The preferable commercial-scale introduction of a lyophilised therapeutic preparation should be highlighted as requiring lesser financial outlay and being easier for the pharmaceutical industry. Stable lyophilised preparations produced according to the present invention are designed for controlled phage therapy of infections and tumours as well as for the production of phage-based pharmaceutical preparations. The production of novel, therapeutically useful phage strains, as well as the production of therapeutic preparations is several times less expensive than the search for novel antibiotics or therapy therewith. The solutions proposed in the present invention are simple, do not require expensive reagents, are based on three different preparations and thus are useful for use in a wider variety of phages.

EXAMPLES

Example 1

Preparation of the Stabilizing Preparation

*Bifidobacterium adolescentis* (PCM 2555) was cultured in a glucose-enriched, semi-liquid corn medium at 37° C. for 48 hours without agitation under microaerophillic conditions. The lyophilised bacterial mass was extracted with 80% aqueous ethanol. Following the removal of cell remnants via centrifugation (3000 RPM, 30 min., 4° C.), the extract was dried to remove the solvent. The remainder was supplemented with aqueous ammonia to a final concentration of 12% and, after 24 hours of mixing at room temperature, centrifuged to remove insoluble material (10000 RPM, 30 min, 4° C.), whereas the aqueous layer was evaporated in a desiccators and the final product was lyophilised.

Example 2

Lyophilisation of K1 Bacteriophages in the Presence of Various Stabilizers

The purified phage preparation was dialysed against PBS buffer with $Ca^{2+}$ and $Mg^{2+}$ ions at 4° C., overnight on a magnetic stirrer. 0.5-1 ml of phage preparation dialysed against PBS were placed into baked, sterile packard vials and ampoules, and then quantities of the stabilizer trehalose, glucose, sorbitol or probiotic extract were added such that the final concentration was 0.1%, 1%, 2%, 4%, 10%, and 20%. All of the solutions were frozen at −70° C. and lyophilised. The preparations in ampoules were lyophilised and stored sealed under vacuum. In such a form, the preparations were stored for several months at 4° C. The samples were then dissolved in 1 ml of milli Q water and phage tires were determined using the RTD method. The control comprised a lyophilised sample of dialysed phage preparation without stabilizers. The phages exhibited no activity in the latter sample. This experiment showed that trehalose and probiotic extract, at 2-4% concentrations, best stabilise phages during lyophilisation.

Example 3

Phage Purification from the Lysate Using Affinity Chromatography in a Column with Immobilised Polylysine An affinity column was prepared with bound polylysine. An agarose gel, such as Sepharose 4B (Pharmacia) (10-20 ml)

was activated using BrCN (Fluka) according to a standard procedure, preferably for 30 minutes at a stable pH=11 at room temperature. Next, excess bromocyanate was eluted out with water and 0.1 M $NaHCO_3$ at pH 8.2. 10 ml of the activated gel were supplemented with 30 mg of polylysine (Sigma) in 5 ml 0.1 M $NaHCO_3$ pH 8.2 and mixed for 2 hours on a rotating mixer. Next, the gel was supplemented with 1 M ethanolamine (POCh) in a volume equal to the gel and the preparation and further mixed for 2 hours at room temperature and then overnight at 4° C. On the next day, the gel was eluted with water and left for 30 minutes at 2 M $K_2HPO_4$, and then eluted with water. Next, the gel suspended in PBS without $Mg^{2+}$ and $Ca^{2+}$ was packed into a glass column (1×10 cm).

A bacteriophge lysate (20 ml) was added onto the affinity column with bound polylysine. After loading the material, the column was eluted with PBS without $Mg^{2+}$ and $Ca^{2+}$. The eluted fractions of 2 ml were evaluated for protein content by measuring absorbance at 280 nm. Following the elution of material unbound to the gel, bacteriophages were eluted using 1 M NaCl in PBS without $Mg^{2+}$ and $Ca^{2+}$ and then the second fraction using 3 M KCNS (Reachim) in PBS without $Mg^{2+}$ and $Ca^{2+}$. Finally, the column was intensively eluted with PBS without $Mg^{2+}$ and $Ca^{2+}$. The material bound to the gel was dialysed against several changes of PBS prior to condensation.

Bibliography

1. Biswas B., Adhya S., Washart P., Brain P., Trostel A. N., Powell B., Carlton R., and Merril C. R. (2002): Bacteriophage therapy rescues mice bacteremic from clinical isolate of vancomycine-resistant *Enterococcus faecium*. Infect. Immun., 204-210
2. Kucharewicz-Krukowska A., Ślopek S. (1987): Immunogenic effect of bacteriophage in patients subjected to phage therapy. Arch. Immunol. Ther. Exp. 35: 553-561
3. Sulakvelidze A., Morris J. G. (2001): Bacteriophages as therapeutic agents. Ann Med. 33(8):507-509
4. Zaremba M. L., Borowski J.: Mikrobiologia lekarska, Warszawa (1997) Wydawnictwo Lekarskie PZWL
5. Ross F. C.: Introductory Microbiology, (1983), Merril C. E. Publishing Co., A. Bell and Howell Company
6. Loeffler J. M., Nelson D., Fischetti V. A. (2001): Rapid killing of *Streptococcus pneumoniae* with bacteriophage cell wall hydrolase. Science 294 (5549):2170-2172
7. Carlton R. M. (1999): Phage therapy: past history and future prospects. Arch. Immunol. Ther. Exp., 47, 267-274
8. Merril C R., Biswas B., Carlton R., Jensen N C., Creed G J., Zullo S. and Adhya S. (1996): Long-circulating bacteriophage as antibacterial agents. Proc. Natl. Acad. Sci. USA 93:3188-3192
9. Górski A., Weber-Dabrowska B., The potential role of endogenous bacteriophages in controlling invading pathogens, Cellular Molec. Life Sci., 62, 2005, 511-519.
10. Lipiński T., Gamian A., Zuziak E., Korzeniowska-Kowal A., Górski A. Oczyszczony preparat bacteriophages y, a method jego of producing and zastosowania, Zgł.. Pat. 381730 z Oct. 2, 2007.
11. Miyamoto-Shinohara Y., Imaizumi T., Sukenobe J., Murakami Y., Kawamura S., Komatu Y. (2000) Survival rate of microbes after freeze-drying and long-term storage. *Cryobiology* 41, 251-255.
12. Hubalek Z. (2003) Protectants used in the cryopresarvation of microorganisms. *Cryobiology* 46, 205-229
13. Lovelock J. E., Bishop M. W. H.(1959) Prevention of freezing damage to living cells by dimetylsulphoxide. *Nature* 183, 1394-1395.
14. Polge C., Smith A. U., Parkes A. S. (1949) Revival of spermatozoa after vitrification and dehydration at low temperatures. *Nature* 164, 666.
15. Nash T. (1966) Chemical constitution and physical properties of compounds able to protect living cells against damage due to freezing and thawing. *Cryobiology*, 179-211
16. Sundberg L., Hoglund S., Purification of T4 phage by adsorption on polylysine agarose, FEBS Letters, 37, (1), 1973, 70-73.
17. Szponar B., Pawlik J. K., Gamian A., Szwajcer-Dey E., Zastosowanie frakcji biał.kowej z mł.óta browarnianego oraz podł.oże mikrobiologiczne, Zgł.. Pat. Nr P-357694 z dn. 11. 12. 2002 r.

The invention claimed is:

1. A process of producing a pharmacologically stable and anticacterially active lyophilised bacteriophage preparation comprising
    a) obtaining purufued bacteriophage;
    b) adding to the purified bacteriophage a probiotic extract, so as to form a bacteriophage preparation,
    wherein the probiotic extract is produced by
        i) contacting a probiotic bacteria strain with an organic solvent to obtain an organic solvent extract;
        ii) drying the organic solvent extract of step i);
        iii) treating the product of step ii) with an ammonia solution to obtain an aqueous layer; and
        iv) isolating the aqueous layer of step iii), so as to thereby produce the probiotic extract; and
    c) lyophilizing the bacteriophage preparation of step b), so as to thereby produce the pharmacologically stabe and antibacterially active lyophilized bacteriophage preparation.

2. The process according to claim 1, wherein the pharmacologically stable and antibacterially active lyophilised bacteriophage preparation is a pharmaceutical preparation and is stable and active at 4° C. for at least 6 months.

3. The process according to claim 1, wherein antibacterial activity of the pharmacologically stable and antibacterially active lyophilised bacteriophage preparation is elevated in biological tests of bacterial lysis, HPLC chromatography, and electrophoresis in the presence of dodecyl sulphate.

4. The process of claim 1, wherein the probiotic bacteria strain is Bifidobacteria.

5. The process of claim 1, wherein the organic solvent is ethanol.

6. The process of claim 2, wherein the pharmaceutical preparation is vacuum lyophilisate in ampoules.

7. The process of claim 2, wherein the pharmaceutical preparation is a tablet.

8. The process of claim 4, wherein the probiotic bacteria strain is *Bifidobacterium adolescentis*.

9. The process of claim 1, wherein the bacteriophage preparation is non-toxic.

10. The process of claim 1, wherein the organic solvent extract of step i) is separated from cell remnants via centrifugation prior to step ii).

11. The process of claim 1, wherein step iv) is performed by centrifuging the aqueous layer extract to remove insoluble material and then removing water by evaporation and lyophilisation.

12. The process of claim 1, wherein the bacteriophage preparation of step b) contains the probiotic extract at a concentration of 2-4%.

13. The process of claim 2, wherein the bacteriophage preparation of step b) contains the probiotic extract at a concentration of 2-4%.

14. The process of claim 4, wherein the bacteriophage preparation of step b) contains the probiotic extract at a concentration of 2-4%.

15. The process of claim 5, wherein the bacteriophage preparation of step b) contains the probiotic extract at a concentration of 2-4%.

16. The process of claim 1, wherein the purified bacteriophage of step a) is in a buffer solution comprising neutral salts.

17. The process of claim 1, wherein the bacteriophage preparation of step b) contains neutral salts.

18. The process according to claim 1, wherein the purified bacteriophage of step a) is obtained by purifying the phages from a bacterial phage lysate in a continuous fashion in an apparatus equipped with a system of selectively permeable ultrafiltration membranes, using lysozyme, a chelator and detergent.

* * * * *